(12) United States Patent
Baecke

(10) Patent No.: US 7,144,473 B2
(45) Date of Patent: Dec. 5, 2006

(54) EVAPORATOR FOR RESPIRATORS AND EVAPORATION METHOD

(76) Inventor: Martin Baecke, Lindenstrasse 7, Dessau (DE) 06847

( * ) Notice: Subject to any disclaimer, the term of this patent is extended or adjusted under 35 U.S.C. 154(b) by 0 days.

(21) Appl. No.: 10/867,604

(22) Filed: Jun. 15, 2004

(65) Prior Publication Data

US 2004/0261951 A1 Dec. 30, 2004

Related U.S. Application Data

(63) Continuation of application No. PCT/DE02/04705, filed on Dec. 20, 2002.

(30) Foreign Application Priority Data

Dec. 22, 2001 (DE) .............................. 101 63 800

(51) Int. Cl.
*B01D 1/00* (2006.01)

(52) U.S. Cl. ................... 159/47.1; 128/204.17; 128/204.18; 128/204.22; 159/16.1; 159/44

(58) Field of Classification Search ............... 159/47.1, 159/44, 16.1, DIG. 1, DIG. 42; 128/204.17, 128/204.18, 204.22
See application file for complete search history.

(56) References Cited

U.S. PATENT DOCUMENTS

| | | | | |
|---|---|---|---|---|
| 3,916,891 A | * | 11/1975 | Freytag et al. ............... | 261/141 |
| 4,026,285 A | * | 5/1977 | Jackson ................. | 128/200.17 |
| 4,028,445 A | * | 6/1977 | Hickmann et al. .......... | 261/142 |
| 4,086,305 A | * | 4/1978 | Dobritz ....................... | 261/30 |
| 4,687,905 A | * | 8/1987 | Cunningham et al. ...... | 392/498 |
| 4,985,122 A | * | 1/1991 | Spencer ........................ | 203/11 |
| 5,348,623 A | * | 9/1994 | Salmon .......................... | 203/1 |
| 6,102,037 A | * | 8/2000 | Koch ..................... | 128/203.26 |
| 6,718,973 B1 | * | 4/2004 | Koch ..................... | 128/203.16 |

FOREIGN PATENT DOCUMENTS

| | | |
|---|---|---|
| DE | 29819950 | 4/1999 |
| DE | 29817685 | 5/1999 |
| DE | 29906911 | 7/1999 |
| DE | 1036499 | 8/1999 |
| DE | 20010553 | 6/2000 |
| DE | 19808590 | 8/2000 |
| DE | 10016005 | 12/2001 |
| DE | 19849571 | 9/2003 |
| GB | 1448473 | 9/1976 |
| SU | 929109 | 5/1982 |

* cited by examiner

*Primary Examiner*—Virginia Manoharan
(74) *Attorney, Agent, or Firm*—King & Schickli, PLLC

(57) ABSTRACT

The present invention relates to an evaporator for respirators, including a storage tank for a liquid, a gas intake flange and a gas outlet flange as well as an apparatus for heating the liquid, which is formed such that it can heat a small portion of the liquid and inject the formed vapor into the gas to be humidified, with the gas to be enriched with the liquid being passed through the upper part of the storage tank over the surface of the liquid, which may be located in the lower part of the storage tank, so as to provide a simple evaporator for respirators having a low consumption of energy. Moreover, the present invention relates to a method of evaporating liquids.

12 Claims, 1 Drawing Sheet

EVAPORATOR FOR RESPIRATORS AND EVAPORATION METHOD

CROSS REFERENCE TO RELATED CO-PENDING APPLICATIONS

This application is a continuation of international PCT application number PCT/DE02/04705 (publication number: WO 03/055555 A1) filed on Dec. 20, 2002 and entitled EVAPORATOR FOR RESPIRATORS AND EVAPORATION METHOD and German patent application number 101 63 800.0-44 filed on Dec. 22, 2001 and entitled VERDAMPFER FÜR BEATMUNGSGERÄTE SOWIE VERFAHREN ZUM VERDAMPFEN the contents of which are expressly incorporated herein by reference.

FIELD OF THE INVENTION

The invention relates to an evaporator for respirators, especially CPAP apparatus, and to an evaporation method for liquids. Evaporators for respirators are e. g. used for the humidification of air.

BACKGROUND OF THE INVENTION

DE 198 08 590 A1 discloses a respiratory humidifier which comprises a hose pump as dosing means and an electrically heated evaporator. The hose pump transports water from a commercially available water bag in the required amount so as to obtain a predetermined relative breathing gas humidity at a predetermined breathing gas temperature. The evaporator makes water at a temperature above 134° C. available, which heats the breathing gas to the predetermined breathing gas temperature when being mixed with the breathing gas to be humidified. Preferably, a thermal insulation is provided between the outlet side of the evaporator and a breathing gas channel in order to avoid, if possible, a heating of the breathing gas channel by the respiratory humidifier also without the supply and evaporation of water. The outlet opening of the evaporator preferably projects into the breathing gas channel. The high heating temperature results from the desire to destroy germs which may exist in the water, since the hygiene provisions for vapor sterilization say that a sufficient germ reduction is achieved if the germs are exposed to a temperature of 134° C. for three minutes.

Respirators also include the so-called CPAP-apparatus which serve the treatment of apneas during the sleep. To this end, the CPAP (continuous positive airway pressure) therapy was developed, which is described in Chest. Volume No. 110, pages 1077–1088, October 1996 and in Sleep, Volume No. 19, pages 184–188. A CPAP-apparatus generates a positive overpressure up to approximately 30 mbar by means of a compressor or turbine and administers the same, preferably via a humidifier, via a hose and via a nose mask, to the respiratory tract of the patient. This overpressure is to ensure that the upper respiratory tract remains fully opened during the whole night, so that no apneas will occur (DE 198 49 571 A1). A humidifier used in conjunction with said CPAP-apparatus prevents the patient's mucous membranes from desiccating.

A breathing gas humidifier for CPAP-apparatus is described in DE 199 36 499 A1. The humidifier comprises a refill unit formed of a tub element and a pot part coupled therewith, which can be removed from a mountable casing. The tub element and the pot part are imperviously connected with each other. In conjunction with a partition wall a storage room for a liquid is formed in said pot part, which contains the major part of the water reserve provided for humidifying the breathing gas. A separate humidifying zone is formed in the tub element disposed underneath the pot part, which merely contains a small portion of the water reserve. The height of the water in the tub element is kept at a predetermined level by a dosing device. In the course of the gradual evaporation of the water located in the tub element water from the liquid storage room is successively or continuously refilled. Via a breathing gas inlet opening the breathing gas is blown through the upper portion of the tub element to a breathing gas outlet opening. The bottom area of the tub element is heated by a heating device. For increasing the thermal transmission, the bottom area of the tub element is made of a material having a high thermal conductivity, e.g. metal.

DE 299 09 611 U1 and DE 200 10 553 U1 likewise describe humidifiers for respirators in which the air is passed over the surface of a heatable water reservoir.

DE 298 19 950 U1 describes in connection with a heatable respiratory humidifier a phase control mechanism and a control circuit for controlling the power supplied to a heating element. The heating element heats a water bath. The control can either be accomplished such that the heating element is supplied with a constant power or that the water bath is kept at a constant temperature.

Documents G-94 09 231.1 and DE 298 17 685 U1 deal with lids for storage vessels for the water reserve of humidifiers for CPAP-apparatus. During operation the lids seal the storage tank in a pressure-proof manner allowing breathing air to be blown through the upper portion of the storage vessel not filled with water, whereby the lid can slightly be opened for refilling water.

It is desirable to provide a simple evaporator for respirators and a simple method, with the evaporator and the method consuming a small amount of energy.

SUMMARY OF THE INVENTION

According to an embodiment of the invention an evaporator for respirators is provided. The evaporator comprises a storage tank for a liquid, a gas intake, a gas outlet and an apparatus for heating the liquid. The apparatus is formed such that it can heat a small portion of the liquid and inject the formed vapor into a gas. The gas intake and the gas outlet are arranged such that the gas is passed through the upper part of the storage tank over the surface of the liquid which may be located in the lower part of the storage tank.

According to another embodiment of the invention a method of evaporating liquids is provided. The method comprises filling a liquid into a storage tank, evaporating a small portion of the liquid, supplying gas, injecting the vapor into the gas, discharging the gas and passing the gas over the surface of the liquid in the storage tank.

An advantage in the invention resides in that, according to the invention, no hose pump is required. Moreover, the passage of the gas enriched with the liquid through the upper part of the storage tank causes a portion of the liquid in the gas being too large to sink down to the liquid reserve, so that a condensation of the liquid downstream of the evaporator, e.g. in respiratory hoses, is largely avoided without any complicated control.

According to the inventive evaporator only an extremely small amount of water is heated. This provides for a very fast operability. The expected heating period is approximately 1 minute. Conventional CPAP-apparatus require between 10 and 30 minutes.

An advantage in the use of a vapor nozzle resides in that the injected vapor is finely distributed in the gas flow. Thus, the gas is more effectively penetrated by the liquid, compared to gas stroking over a liquid surface.

The humidification of air constitutes the most frequent case of application.

An advantage in the use of a regulating reservoir resides in that the operating mode of the evaporator is not dependent on the filling level of the liquid in the storage tank. Due to the control valve the handling and the operating mode of the evaporator resemble a coffee machine, which results in a high acceptance and a fast familiarity by the patient.

The advantage of a resistance heater resides in the low price, the universal availability of electricity at least in the industrial countries as well as in the easy control of the heating capacity, e.g. by a phase control mechanism.

An optimum exploitation of the available heating capacity is given, as the surfaces for a dissipation of heat to the environment are kept small by the use of a heating channel and a thermal bridge. Therefore, the heater may be designed very economically as far as the energy consumption is concerned, so that the method is basically suited for applications in mobile apparatus with a temporarily self-contained operation.

An advantage in a pressure-proof sealing of the storage tank by a lid resides in that the gas is supplied and discharged in a defined manner, whereby only the intake flange or the outlet flange have to be connected to a pumping device, i.e. to a turbine, for example.

BRIEF DESCRIPTION OF THE DRAWINGS

In the following, preferred embodiments of the invention will be explained in more detail with reference to the attached drawing, wherein.

DETAILED DESCRIPTION OF THE INVENTION

Figure 1:
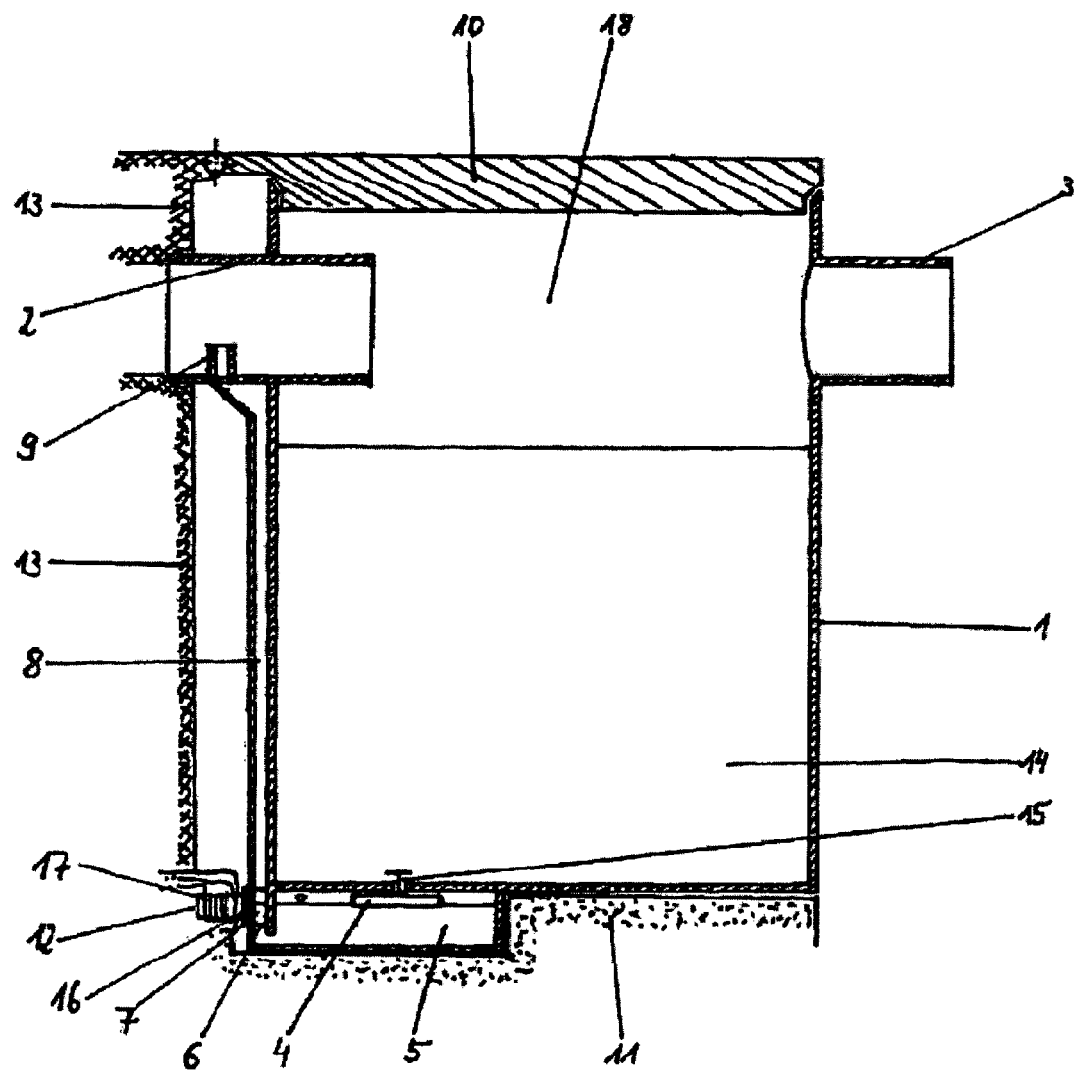
FIG. 1 shows an embodiment of the evaporator according to the invention.

The essential components of the evaporator are: storage tank 1 with intake flange 2, outlet flange 3, regulating reservoir 5 with control valve 4 floating in the regulating reservoir, heating channel 6, heating zone 7, vapor channel 8, vapor nozzle 9, lid 10 and foot 11 with contact 12.

A larger amount of liquid 14—preferably water—is contained in the storage tank 1. A portion of the liquid 14 flows through the opening 15 in the bottom of the storage tank 1 into the regulating reservoir 5 and the heating channel 6 communicating with the same. The control valve 4 preferably operates as a float and closes the opening 15 if the liquid level in the regulating reservoir 5 is high enough. As shown in the drawing, the control valve 4 is also operable to at least partially fill a channel 8 that supplies vapor to the gas with liquid from the storage tank 1 via the regulating reservoir 5. As should be appreciated from viewing this drawing, liquid flow from the storage tank 1 to the vapor channel 8 is stopped by the control valve 4 as soon as the liquid level reaches a predetermined level, since the valve operates as a float and closes the opening 15. The heating zone 7 is provided in the heating channel 6, which as shown in the drawing is in the lowermost end of and forms part of the vapor channel 8. A preferably metallic thermal bridge 16 transfers the heat generated by an electric resistance heater 17 to the liquid in the heating zone 7. According to a preferred embodiment the thermal bridge is thereby electrically insulated from the resistance heater 17. The heating zone is preferably separated from the liquid by a nonstick layer so as to avoid the deposition of impurities of the liquid. When water is used, the nonstick layer particularly reduces the calcification tendency of the heating zone 7. According to another embodiment the heating filament forming the resistance heater may directly be wound around the heating channel being, as compared to the heating filament, electrically insulated, so that a metallic thermal bridge may be waived.

By the arrangement of the heating zone 7, only the uppermost liquid layer standing in the heating channel 6 is heated up to evaporation. The vapor from the liquid in this heating channel 6 rises upwardly through the vapor channel 8 and is finely distributed by the vapor nozzle 9 in the air intake flange 2. Preferably from a respirator 13 is the fresh air flow passed either directly or by means of a non-illustrated hose through the intake flange 2 into the gas volume 18 of the storage tank 1. The gas flow thereby entrains the finely distributed vapor in the intake flange 2. From the gas flow so abundantly enriched with the liquid, excess vapor is precipitated in the form of fog droplets. Due to the relatively cooler environment and the clearly smaller flow rate in the air volume 18 these fog droplets sink downwardly into the liquid 14 and are available again for an evaporation at a later time. The gas flow optimally enriched with the liquid escapes from the storage tank 1 via the air outlet flange 3. A respiratory hose is normally connected to the outlet flange 3, which conducts the humidified air towards the patient. The storage tank 1 is sealed with a lid 10 in a largely gas-proof manner. The expression "largely gas-proof" implies that leak flows preferably resulting from leaks between the lid 10 and the storage tank 1 are small as compared to the gas flow through the outlet flange 3. The gas flow through leaks can thereby reach up to approximately 20% of the gas flow through the outlet flange 3.

For filling the storage tank 1 with liquid the lid 10 is opened and the storage tank 1 is lifted out of the foot 11. In case of a stand-alone evaporator or respiratory humidifier the foot 11 forms a separate component which provides the voltage supply for the resistance heater 17 via the contacts 12. In case of an integrated evaporator or respiratory humidifier the foot 11 forms part of the respirator 13.

The cleaning may be accomplished with decalcifying agents. If necessary, the bottom of the regulating reservoir may be designed to be detachable. In this case, cleaning in the dishwasher is sensible. The storage tank 1 is made of a transparent plastics material and allows a visual filling level control up to nearly the complete water consumption.

As was mentioned above, the power control for the electrical power transformed into thermal energy in the resistance heater 17 is preferably effected by a phase control mechanism. The power can preferably be adjusted on a potentiometer. The scale for the potentiometer may indicate optional units, percentages of the maximum power or the power in watt.

Moreover, a sensor for the portion of the liquid in the gas, i.e. a humidity sensor according to the preferred embodiment, may be provided in the outlet flange 3. If such a sensor is provided, the heating capacity is preferably controlled such that the liquid portion in the gas is constant, i.e., for example, that the relative air humidity remains constant. In the embodiment comprising such a sensor, too, can the desired portion of the liquid in the gas, i.e., for example, the relative air humidity, be predefined by a potentiometer. The scale of the potentiometer may, according to this embodiment, indicate either optional units or, for example, the air humidity in percent.

Preferably when the humidifier forms part of a respirator controlled by a micro-controller, can the potentiometer by replaced by a digital/analog converter connected to the micro-controller. The input of the voltage value outputted by the digital/analog converter is preferably performed via the keys provided for controlling the micro-controller.

According to a simple embodiment the resistance heater 17 made of a PTC resistor without any controlling possibility may be connected to a largely constant voltage, e.g. the supply voltage of an alternating voltage of 110 or 220 V. According to this embodiment the enrichment of the gas with the liquid is substantially codetermined by the temperature of the water reservoir, which deviates only slightly from the ambient temperature. This embodiment is sensible, above all, because the bedroom temperature is in a narrow range of about 17° C. in most cases.

According to another embodiment the power control may be accomplished in dependence on a flow signal supplied by a respirator. If the flow is high, the heating capacity is increased since, due to the higher flow, also a larger quantity of air has to be humidified.

In connection with the power control depending on a flow signal it is particularly advantageous to use a heater with a small mass and, therefore, with a small thermal inertia. Thus, it becomes possible that the heating takes place exclusively while the patient inhales. In this manner heating capacity is saved, as—in the optimum case—merely the air inhaled by the patient is humidified. Moreover, a mass-impregnated and drained heater, and thus a fast heater, can produce the operability of the evaporator within the breathing cycle and, therefore, within split seconds.

The air exhaled by the patient need not be humidified. During the breathing, the air in the patient's lung is further enriched with humidity and heated approximately to the body temperature. Thus, the exhaled air generally has a higher absolute humidity than the inhaled air. Especially when using an evaporator according to the invention for a CPAP-apparatus it may occur during the exhalation that air is pressed from the outlet flange 3 via the air volume 18 to the intake flange 2 and further into the respirator 13 or a hose between the respirator 13 and the evaporator.

The respirator 13 or a hose between the same and the evaporator, has a room temperature between 16° and 20°, which is clearly lower than the body temperature of 36° C. Therefore, there is the danger that humidity of the exhaled air condenses in the respirator 13 or the hose. The tendency towards condensation is increased if both inhaled and exhaled air is humidified via the vapor nozzle 9. Humidity in the respirator or the hose is a culture medium for microorganisms, such as fungi. Under this microbiological aspect, too, it is advantageous if merely the inhaled air is humidified.

The subsequent humidification of the inhaled air supports the condensation of excess vapor in the air volume 18 and thus a feedback of excess vapor into the liquid 14.

In the foregoing, the invention was explained in more detail by means of preferred embodiments. The person skilled in the art will appreciate, however, that different modifications may be made without departing from the spirit of the invention. Therefore, the scope of protection will be defined by the following claims and their equivalents.

LIST OF REFERENCE NUMERALS 1 storage tank
2 intake flange
3 outlet flange
4 control valve
5 regulating reservoir
6 heating channel
7 heating zone
8 vapor channel
9 vapor nozzle
10 lid
11 foot
12 contact
13 respirator
14 liquid
15 opening
16 thermal bridge
17 resistance heater
18 air volume

What is claimed is:

1. An evaporator for respirators, comprising:
a storage tank comprising a lower part filled with a liquid during operation and an upper part filled with a gas during operation;
a gas intake connected to said upper part of said storage tank;
a gas outlet connected to said upper part of said storage tank, said gas intake and said gas outlet arranged such that the gas passes through said upper part of the storage tank over the surface of the liquid;
a regulating reservoir connected to the lower part of the storage tank by a control valve;
a vapor channel connecting the regulating reservoir to said gas intake, said regulating reservoir communicating with said vapor channel, and said control valve operable to at least partially fill the vapor channel with liquid from the storage tank;
a heater for heating a small portion of the liquid within the vapor channel to form a vapor injected into said gas intake through the vapor channel; and
a vapor nozzle connected to said vapor channel and adjacent the gas intake so that it may inject the vapor into the gas.

2. The evaporator according to claim 1, wherein the liquid is water and the gas is air.

3. The evaporator according to claim 1, wherein the heater is formed by a resistance heater and a thermal bridge, with the thermal bridge electrically insulating the resistance heater from the liquid to be heated and simultaneously thermally contacting the liquid.

4. The evaporator according to claim 1, wherein the evaporator forms part of a respirator associated with a continuous positive airway pressure (CPAP) apparatus.

5. The evaporator according to claim 1, wherein a detachable lid seals the storage tank such that less gas leaks through the seal than passes through the outlet.

6. The evaporator according to claim 1, wherein a hinged lid seals the storage tank such that less gas leaks through the seal than passes through the outlet.

7. A method of evaporating liquids, comprising:
filling a liquid into a storage tank;

filling a lower part of a vapor channel via a control valve and a regulating reservoir with liquid from said storage tank;

stopping the liquid flow from said storage tank to said vapor channel by said control valve as soon as the liquid level within said vapor channel has reached a predetermined level;

heating the liquid within said vapor channel thereby evaporating a portion of the liquid within said vapor channel;

supplying gas;

injecting the vapor generated by said heating into the supplied gas using a vapor nozzle;

passing the supplied gas together with the injected vapor over the surface of the liquid in the storage tank; and discharging the gas passed over the surface of the liquid in the storage tank.

8. The method according to claim 7, wherein the liquid for the filling step is water and the gas for the supplying step is air.

9. The method according to claim 7, wherein the heating step comprises using a resistance heater and a thermal bridge, the thermal bridge electrically insulating the resistance heater from the liquid to be heated and simultaneously thermally contacting the liquid.

10. The method according to claim 7, further including the step of delivering the gas to a continuous positive airway pressure (CPAP) patient.

11. The method according to claim 7, further including the steps of sealing the storage tank with a detachable lid such that less gas leaks through the seal than is discharged, and opening the lid to fill the storage tank with liquid.

12. The method according to claim 7, further including the steps of sealing the storage tank with a hinged lid such that less gas leaks through the seal than is discharged, and swinging the lid open to fill the storage tank with liquid.

* * * * *